United States Patent
Takeshima

(10) Patent No.: US 7,605,587 B2
(45) Date of Patent: Oct. 20, 2009

(54) MAGNETIC RESONANCE IMAGING APPARATUS

(75) Inventor: Hirotaka Takeshima, Ibaraki (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 11/791,878

(22) PCT Filed: Nov. 29, 2005

(86) PCT No.: PCT/JP2005/021835

§ 371 (c)(1),
(2), (4) Date: May 29, 2007

(87) PCT Pub. No.: WO2006/057395

PCT Pub. Date: Jun. 1, 2006

(65) Prior Publication Data

US 2008/0061787 A1    Mar. 13, 2008

(30) Foreign Application Priority Data

Nov. 29, 2004    (JP) .............................. 2004-343660

(51) Int. Cl.
*G01V 3/00* (2006.01)

(52) U.S. Cl. ..................................... 324/307

(58) Field of Classification Search .......... 324/300–322
See application file for complete search history.

(56) References Cited

U.S. PATENT DOCUMENTS

| | | | |
|---|---|---|---|
| 5,561,371 | A | 10/1996 | Schenck |
| 5,638,595 | A | 6/1997 | Repinski et al. |
| 6,531,870 | B2 * | 3/2003 | Heid et al. .................. 324/318 |
| 6,903,552 | B2 * | 6/2005 | Dietz et al. .................. 324/318 |
| 6,930,482 | B2 * | 8/2005 | Heid et al. ................... 324/318 |
| 7,026,816 | B2 * | 4/2006 | Gebhardt et al. ............. 324/318 |
| 7,126,334 | B2 * | 10/2006 | Heid ........................... 324/318 |
| 7,235,974 | B2 * | 6/2007 | Nistler et al. ................ 324/318 |
| 7,239,141 | B2 * | 7/2007 | Nistler et al. ................ 324/318 |
| 7,375,526 | B2 * | 5/2008 | Edelstein et al. ............. 324/318 |

FOREIGN PATENT DOCUMENTS

| | | |
|---|---|---|
| JP | 63-1008 | 1/1988 |
| JP | 3-210236 | 9/1991 |
| JP | 9-168525 | 6/1997 |
| JP | 9-182732 | 7/1997 |
| JP | 10-328159 | 12/1998 |
| JP | 2000-166896 | 6/2000 |
| JP | 2003-164432 | 6/2003 |
| WO | WO03/062846 A2 | 7/2003 |

* cited by examiner

*Primary Examiner*—Brij B. Shrivastav
*Assistant Examiner*—Dixomara Vargas
(74) *Attorney, Agent, or Firm*—Cooper & Dunham, LLP

(57) ABSTRACT

A magnetic resonance imaging apparatus is provide that includes static magnetic field generation means arranged around an imaging space where an examinee is to be located and generating a static magnetic field in the imaging space; gradient magnetic field generation means arranged in the imaging space side of the static magnetic field generation means and generating a gradient magnetic field in the imaging space; and high-frequency magnetic field generation means arranged at the imaging space side of the gradient magnetic field generation means and generating a high-frequency magnetic field in the imaging space. The gradient magnetic field generation means has a concave portion in the vicinity of the imaging space depressed toward the static magnetic field generation means. At least a part of the high-frequency magnetic field generation means is contained in the concave portion.

19 Claims, 7 Drawing Sheets

MAGNETIC RESONANCE IMAGING APPARATUS

TECHNICAL FIELD

This disclosure relates to a magnetic resonance imaging apparatus (hereinafter referred to as an MRI apparatus), in particular to a technique for improving opened structure of the MRI apparatus.

BACKGROUND ART

In MRI apparatus, it is important to improve its open structure for the purpose of reducing fear of confined spaces of an examinee. In Patent Document 1, an example of providing a concave in the center section on the side of the surface facing imaging space of which two cooling containers are arranged above and under the imaging space facing each other, and disposing a main coil of gradient magnetic coil and a shielding coil in the concave thereof is described. In accordance with this prior art, gradient magnetic field coils can be effectively disposed using a concave space provided in the cooling containers. By such configuration, it is possible to provide an MRI apparatus with highly opened structure, since distance between the gradient magnetic field coils disposed facing each other above and below an examinee is extended whereby providing larger space for placing the examinee.

Patent Document 1: JP-A-H9-262223

However, in the prior art described in Patent Document 1, while alignment of superconducting magnets or gradient magnetic field coils are optimized, attention is not paid to the alignment of irradiation coils.

BRIEF SUMMARY

In an aspect of this disclosure, there is provided an MRI apparatus with further improved opened construction.

In an exemplary embodiment of this disclosure, there is provided a MRI apparatus comprising:

static magnetic field generation means arranged around an imaging space where an examinee is placed, and is for generating a static magnetic field in the imaging space;

gradient magnetic field generation means arranged in the imaging space side of the static magnetic field generation means, and is for generating a gradient magnetic field in the imaging space; and high-frequency magnetic field generation means arranged at the imaging space side of the gradient magnetic field generation means, and is for generating high-frequency magnetic field in the imaging space, wherein the gradient magnetic field generation means has a concave portion in the vicinity of the imaging space depressed toward the static magnetic field generation means, containing at least a part of the high-frequency magnetic field generation means in the concave portion.

BRIEF DESCRIPTION OF THE DIAGRAMS

BEST MODE FOR CARRYING OUT THE INVENTION

Figure 1:
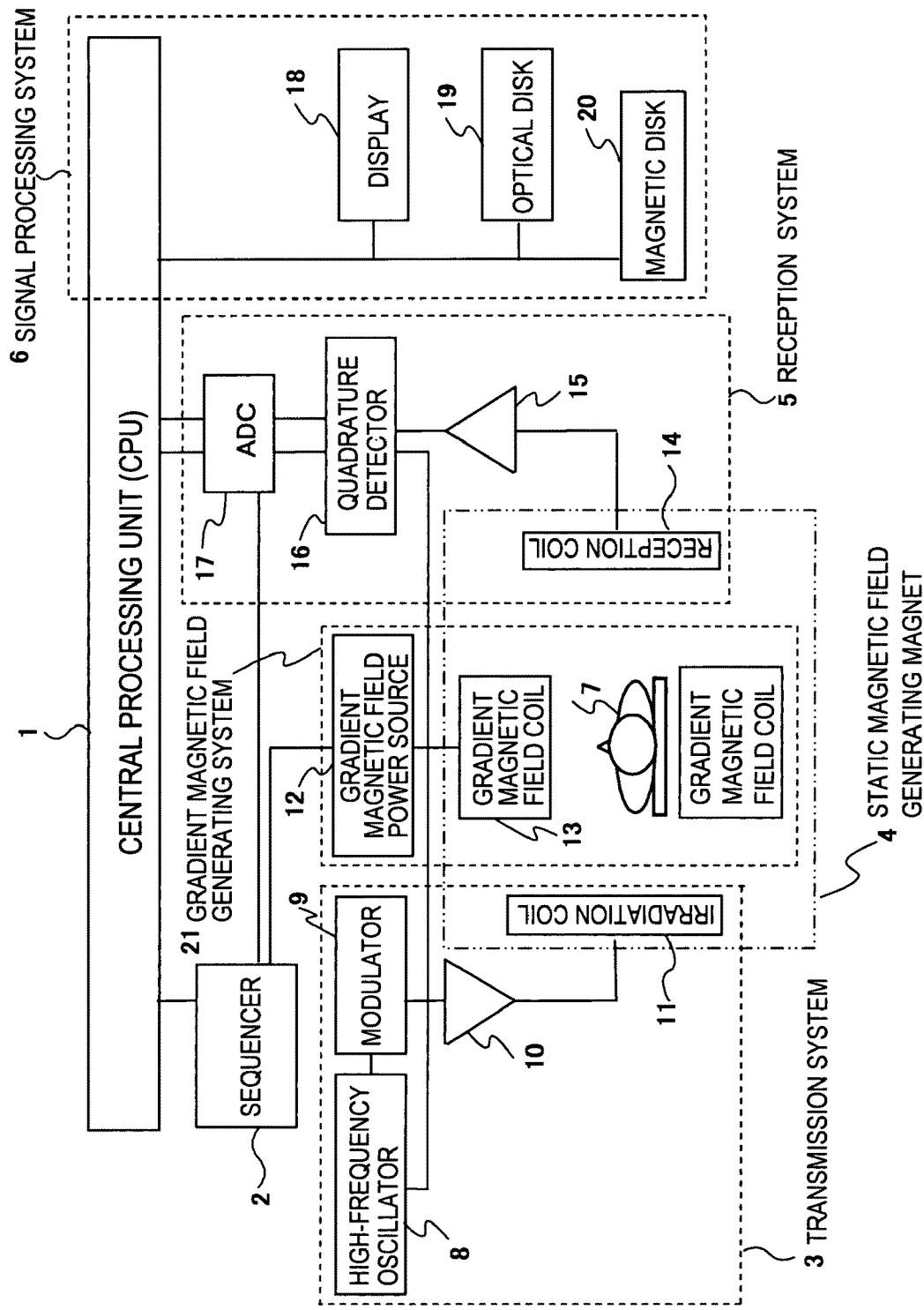
FIG. 1 is a general system configuration of an MRI apparatus.

Hereinafter, system configuration of an MRI apparatus will be described in detail.

Configuration of an MRI apparatus can be classified broadly into central processing unit (hereinafter referred to as CPU) 1, sequencer 2, transmission system 3, static magnetic field generation magnet 4, reception system 5, gradient magnetic field generation system 21, and signal processing system 6.

CPU 1 controls sequencer 2, transmission system 3, reception system 5 and signal processing system 6 according to the program set in advance. Sequencer 2 operates based on the control command from CPU 1, and is caused to transmit a variety of commands necessary for collecting image data of fault planes of examinee 7 to transmission system 3, gradient magnetic field generation system 21 and reception system 5.

The transmission system 3 comprises devices such as high-frequency oscillator 8, modulator 9, irradiation coil 11 and RF shield, and irradiates predetermined pulsing electromagnetic waves to the examinee by performing amplitude modulation on the reference high-frequency pulse from high-frequency oscillator 8 by modulator 9, amplifying the amplitude modulated high-frequency pulse via high-frequency amplifier 10 and providing them to irradiation coil 11.

Static magnetic field magnet 4 is for generating a homogeneous static magnetic field around examinee 7 in a predetermined direction. Irradiation coil 11, gradient magnetic field coil 13 and reception coil 14 are disposed inside of the static magnetic field magnet 4. Gradient magnetic field coil 13 is included in gradient magnetic field generation system 21, receives provision of electric current from gradient magnetic field power source 12, and causes to generate gradient magnetic field under the control of sequencer 2.

Reception system 5 is for detecting high-frequency signals (NMR signals) discharged by nuclear magnetic resonance of atomic nuclei of biochemical tissue of the examinee, having reception coil 14, amplifier 15, quadrature detector 16 and A/D converter 17. High-frequency signals (NMR signals) responded from the examinee by electromagnetic waves irradiated from above-mentioned irradiation coil 11 are detected by reception coil 14 arranged in contiguity with the examinee, inputted to A/D converter 17 via amplifier 15 and quadrature detector 16, converted into digital quantity, and transmitted to CPU 1.

Signal processing system 6 comprises an external storage such as magnetic disk 20 and optical disk 19 and display 18 having a device such as CRT. When data from reception system 5 is inputted to CPU 1, CPU 1 executes processes such as signal processing or image reconstruction, displays images of the desired cross sections of examinee 7 which are the result of the previously mentioned processes on display 18, and stores the images to a device such as magnetic disk 20 of the external storage.

Embodiment 1

Figure 2:
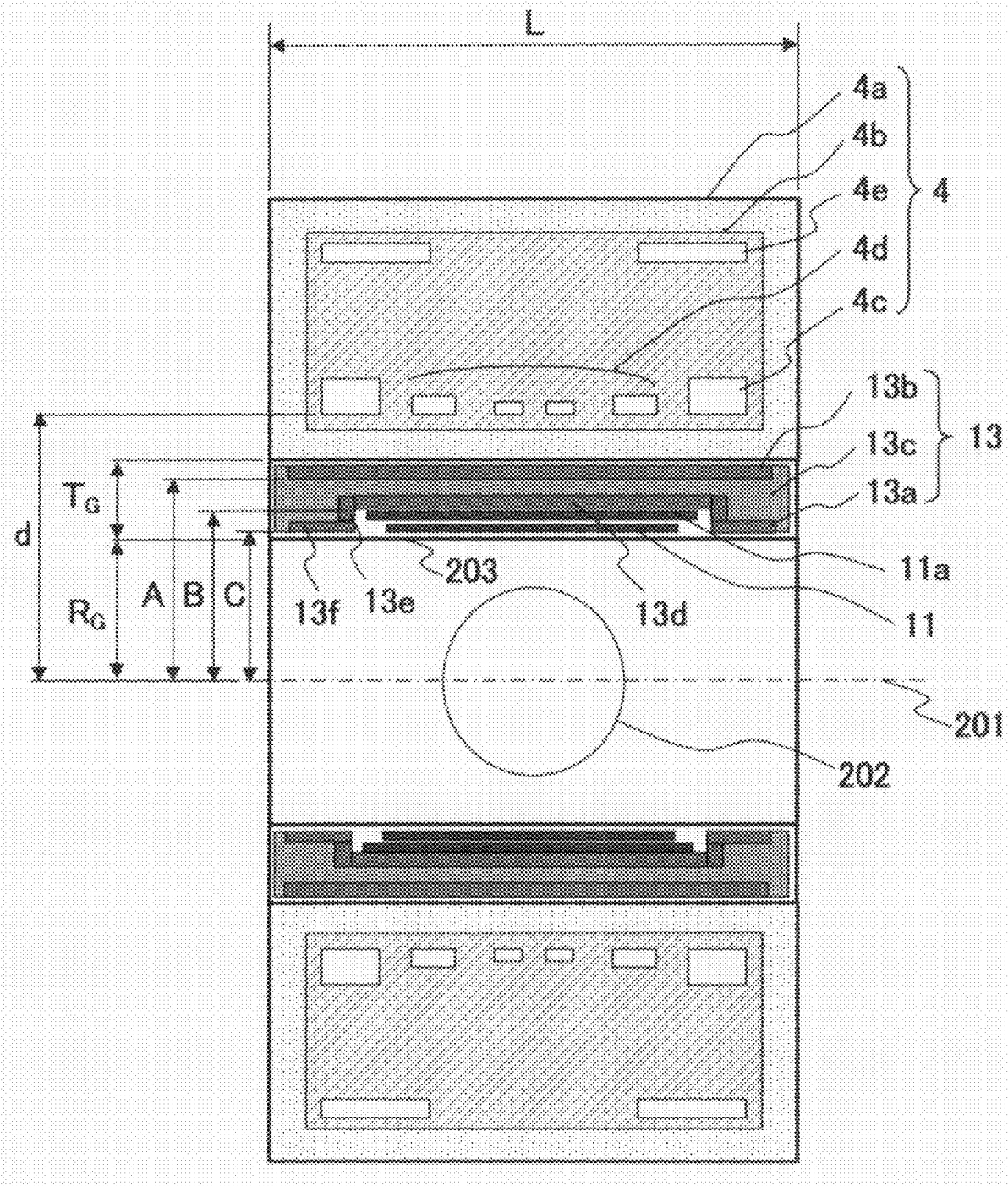
FIG. 2 is a diagram showing a cross section of a horizontal magnetic field type MRI apparatus relating to embodiment 1 of the present invention.

FIG. 2 is a diagram showing a cross section of a horizontal magnetic field type MRI apparatus (tunnel type) relating to embodiment 1 of the present invention. In FIG. 2, 4 is a static magnetic field generation magnet, and is for generating static magnetic field having high uniformity in the center of imaging space 202 by arranging a plurality of concentric superconducting coils as having Z-axis 201 in horizontal direction. Static magnetic field generation magnet 4 comprises vacuum case 4a forming a donut shape, helium container 4b disposed in vacuum case 4a, coils such as main coil 4c, uniformity controlling coil 4d and shielding coil 4e arranged in helium container 4b. Main coil 4c is for generating main static magnetic field to imaging space 202, uniformity controlling coil 4d is for improving uniformity of static magnetic field generated by main coil 4c, and shielding coil 4e is for restraining the magnetic field from leaking to the outside of the gantry. Also, though not shown in the diagram, a heat shield is provided on the outside of helium container 4b in vacuum case 4a, and a cooing machine is provided to re-condense the liquid helium evaporated in the helium container.

Also in FIG. 2, 13 is a gradient magnetic field coil, and is formed by components such as gradient magnetic field main coil 13a for generating main gradient magnetic field to imaging space 202, gradient magnetic field shielding coil 13b arranged on the side of static magnetic field generation magnet 4 of gradient magnetic field main coil 13a and is for preventing unnecessary eddy current to be carried to vacuum case 4 and other parts forming static magnetic field generation magnet 4 due to the leakage of magnetic field generated by gradient magnetic field main coil 13a which causes negative effect, and intermediate member 13c for maintaining the spacing between gradient magnetic field main coil 13a and gradient magnetic field shielding coil 13b.

Further, gradient magnetic field main coil 13a in the present embodiment is formed by bottom potion 13d, coupling potion 13e and edge portion 13f, and the central portion (bottom portion 13d) near imaging space 202 is depressed toward the side of static magnetic field generation magnet 4. In the depressed portion, irradiation coil 11, and RF shield 11a which is imposed in the back surface of irradiation coil 11 and is for preventing negative effects caused by electromagnetic waves generated by irradiation coil 11 interfering with parts such as gradient magnetic field coil 13, are completely contained.

In the present embodiment, irradiation coil 11 is formed by components such as electric conductor, to be the current path, and capacitor elements. Also, RF shield 11a is formed by a board for shielding high-frequency radiation, and irradiation coil and RF shield are mechanically connected by an intermediate member for the irradiation coil (not shown in the diagram). Generally the intermediate member for the irradiation coil has 10~15 mm thickness.

In order to completely contain irradiation coil 11, RF shield 11a or the intermediate member for irradiation coil in the concave portion of gradient magnetic field main coil 13a, measures are taken to, for example, segment each of them by 180 degrees, arrange them in predetermined positions and connect necessary parts. Or, manufacturing method measures can also be taken by piling up the gradient magnetic field coils around the irradiation coil that is manufactured first.

Figure 3:
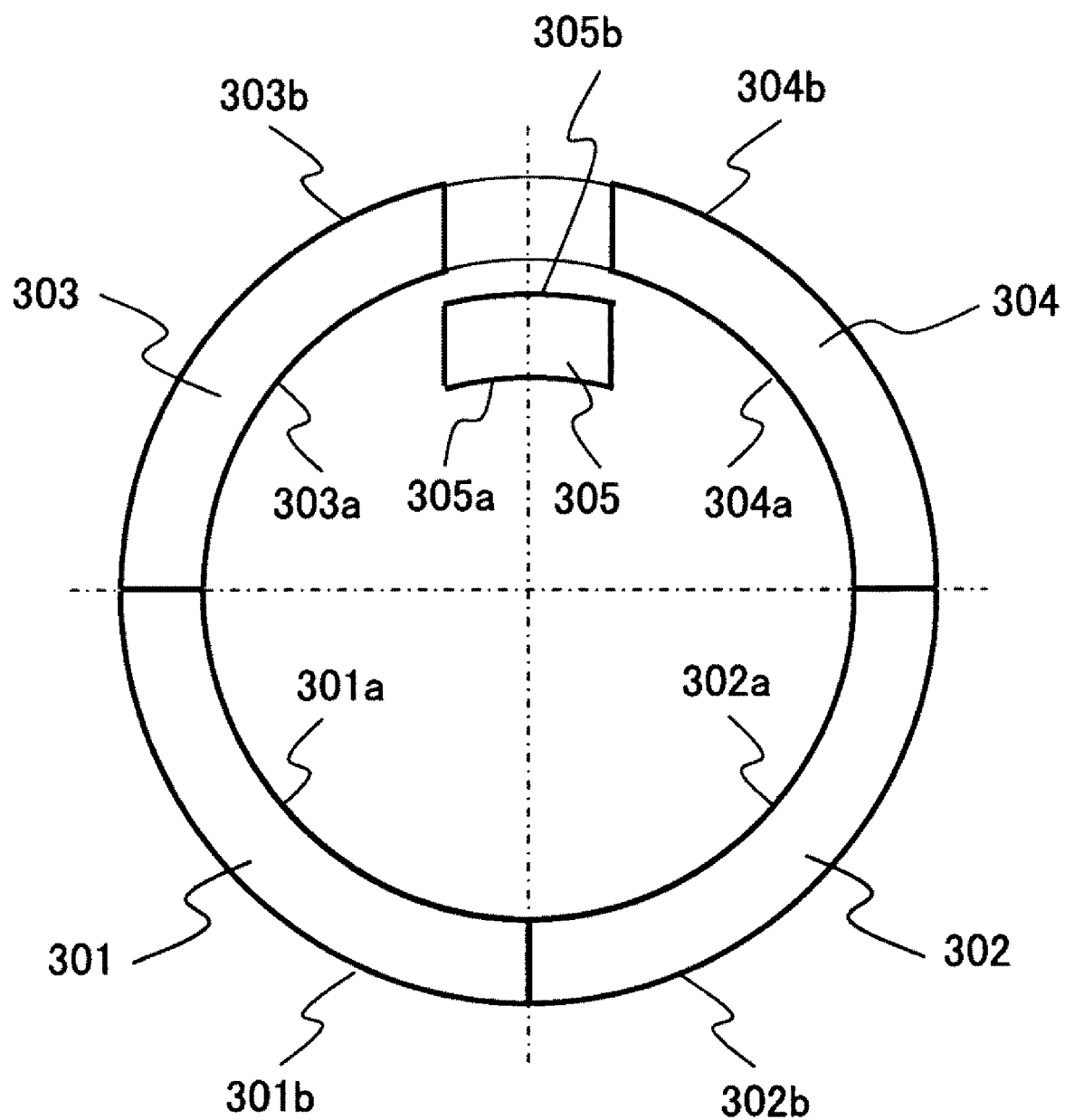
FIG. 3 is a diagram showing a condition of an intermediate member of RF coil being segmented into a plurality of pieces and embedded in the concave of a gradient magnetic field coil.

Also, as shown in FIG. 3, the intermediate member for the irradiation coil may segmented into a plurality of pieces (301~305) and embedded in the concave of the gradient magnetic field coil. In such configuration shown in FIG. 3, a flexible substrate by which a part of a circuit is cut and made into a planar form (foldable) is used for the body of the irradiation coil with the attachments such as a condenser or inductor (301a~305a). A circuit can be configured through attaching the body of irradiation coil to the intermediate member and connecting the cut section by a technique such as soldering. Also, an RF shield is generally flexible, formed by a material such as copper foil or copper mesh, and is configured to attach the cut portion of the material to areas such as the inner periphery surface of the gradient magnetic coil or the outer periphery surface of the intermediate member for irradiation coil (for example, 301b~305b).

More concrete description on the configuration of gradient magnetic field main coil 13a and gradient magnetic field shielding coil 13b referring to FIG. 2 is as follows. Imaging space 202 side of vacuum case 4a basically forms a cylinder shape, and gradient magnetic field shielding coil 13b forms a cylinder shape along with previously mentioned cylinder shape and has a predetermined internal radius (hereinafter referred to as A). Further, gradient magnetic field main coil 13a is formed by cylinder shape conductor parts (13d and 13f) having internal radius B or C which is smaller than the internal radius A, and coupling portion 13e for connecting those parts. Here, a part having internal radius C is imposed more on the outside than the part having internal radius B with respect to imaging space 202 in Z-axis 201 direction, and internal radius C is made smaller than internal radius B.

Generally in MRI system, the whole magnet is covered by a gantry cover. In this case, the radius of the internal periphery surface of the gantry cover of the side facing imaging space 202 (distance shown by $R_G$ in FIG. 2) is an important value for defining the open construction of the gantry.

In the present embodiment of the horizontal magnetic field type MRI apparatus, gradient magnetic field main coil 13a is formed by bottom portion 13d positioned near imaging space 202 in Z-axis 201 direction, edge portion 13f positioned far from imaging space 202, and coupling portion 13e for connecting bottom portion 13d and edge portion 13f, and bottom portion 13d is imposed to a position closer to static magnetic field generation magnet 4 compared to edge portion 13f (position distant from Z-axis 201).

With this configuration, irradiation coil 11 and RF shielding coil 11a can be contained in the cylinder shape conductor part 13d having a large radius. As a result, the spacing between the surface of imaging space 202 side of static magnetic field generation magnet 4 and the surface 203 of imaging space 202 side of the gantry cover (distance shown by $T_G$ in FIG. 2) can be narrowed, compared to the conventional case that both gradient magnetic field main coil 13a and gradient magnetic field shielding coil 13b are flat plate. In other words, if the internal periphery surface of static magnetic field generation magnet 4 ($T_G+R_G$) is the same size, $T_G$ can be narrowed only by the thickness portion of irradiation coil 11 and RF shielding coil 11a. As a result, since bore radius (distance shown by $R_G$ in FIG. 2) can be extended, opened construction of the MRI apparatus can be improved.

Also, if the size of $R_G$ is to set as the same size of a conventional apparatus, coils 4c and 4d in static magnetic field generation magnet 4 can be imposed closer to imaging space 202 side by the portion that $T_G$ is narrowed. In other words, since radius d can be made smaller, static magnetic field with stronger intensity can be generated with the same degree of current value as the conventional apparatus. Conversely, if intensity of the static magnetic field is about the same, less current value is required to be applied.

Furthermore, shaft length (L) of static magnetic field generation magnet 4 can be shortened. Generally, the smaller the prospective angle formed by the superconducting coil and z-axis 201 as seen from the center of uniform magnetic field region 202 is made, the easier it is to generate favorable magnetic field homogeneity. Therefore, when magnetic homogeneity is kept constant, the smaller the coil radius d is made, the more axis length L of the coil can be shortened until the above-mentioned prospective angle reaches to a predetermined angle. As a result, the axis length of the gantry can be shortened, whereby enabling improvement of the opened construction of the apparatus. For example, when size of the coil is L=1 m and 2d=1 m, L can be shortened about 5 cm by making 2d 5 cm shorter. In view of this, such configuration of gradient magnetic field coil 13 in the present embodiment is especially effective in a horizontal magnetic field type MRI apparatus having a short bore (e.g. axis length (L) of 1300 mm and below) with which the axis length (the length shown by L in FIG. 2) is shortened and the opened construction is improved. In addition, while coupling portion 13e in FIG. 2 is illustrated to have a surface vertical to Z-axis 201, it may be tapered as need arises.

In the present embodiment, since the distance between irradiation coil 11 and RF shielding coil 11a can be set as about the same as the conventional apparatuses, magnetic field generation efficiency of irradiation coil 11 can be sufficiently improved. Also, in regard to the gradient magnetic field coil, since the internal radius of cylindrical conductor portion 13f is normally smaller with respect to end portion 13f in the outside of Z-axis 31 direction having higher density than bottom portion 13d on the inside of Z-axis 201 direction near imaging space 202, negative influence over gradient magnetic field generation efficiency can be reduced.

Figure 4:
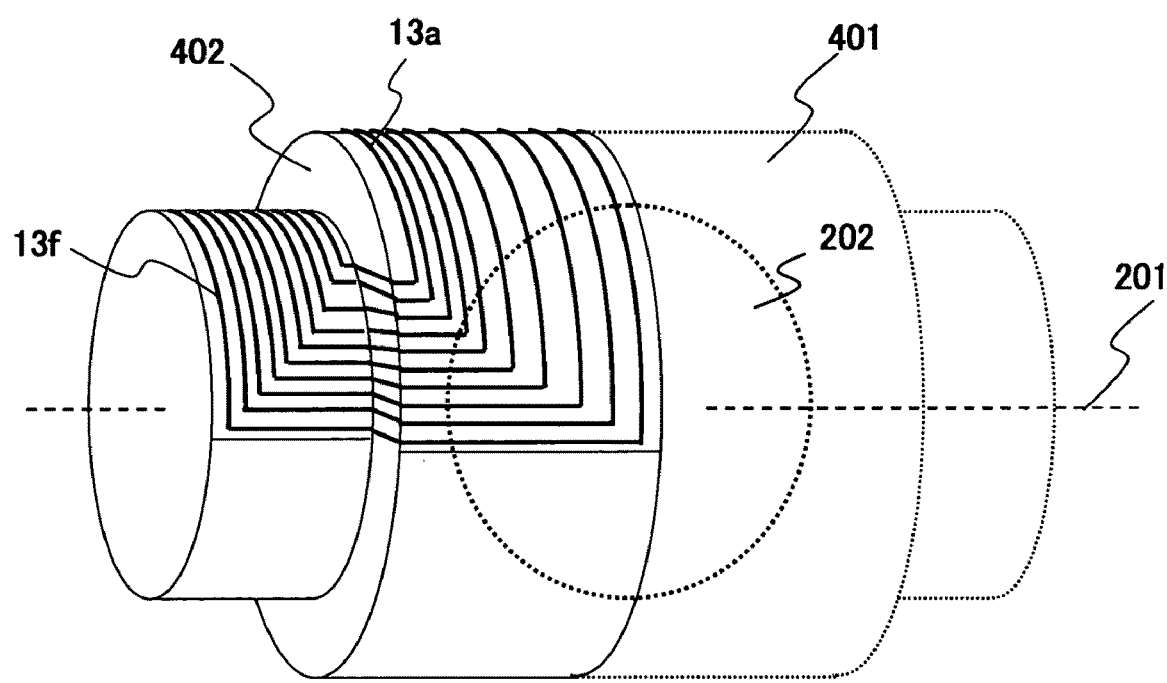
FIG. 4 is a schematic view showing a coil pattern of gradient magnetic field main coil 13a in X or Y direction in embodiment 1.

FIG. 4 is a schematic view showing a coil pattern of gradient magnetic field main coil 13a for X or Y-direction in the present embodiment. Coil pattern is formed vorticosely, and the current density is high in the outside of Z-axis direction apart from imaging space 202 (in other words, the spacing between adjacent conducting wires of the coil pattern is short). In the present embodiment, as seen in FIG. 4, gradient magnetic field main coil 13 is configured that the coil is attached on the outside of container-like object 401 by which cylinders with different radii are combined. In the example of FIG. 4, magnetic field generation efficiency of gradient magnetic field coil 13 is made higher through making the size of end portion 13f as large as possible by arranging the central portion of the vorticose coil pattern in the vicinity of portion 402 being a bump due to combining the cylinders with different radius. In this regard, however, the portion being a bump does not have to be the center of the vorticose coil pattern. When the bump portion is apart from the center of the vorticose coil pattern, there is an advantage in improving the characteristic of the generated gradient magnetic field since the number of coils attached to the bump portion is reduced, or in facilitating the manufacture since the number of conducting wires for connecting cylindrical conductor portions 13d and 13f is reduced.

Embodiment 2

Figure 5:
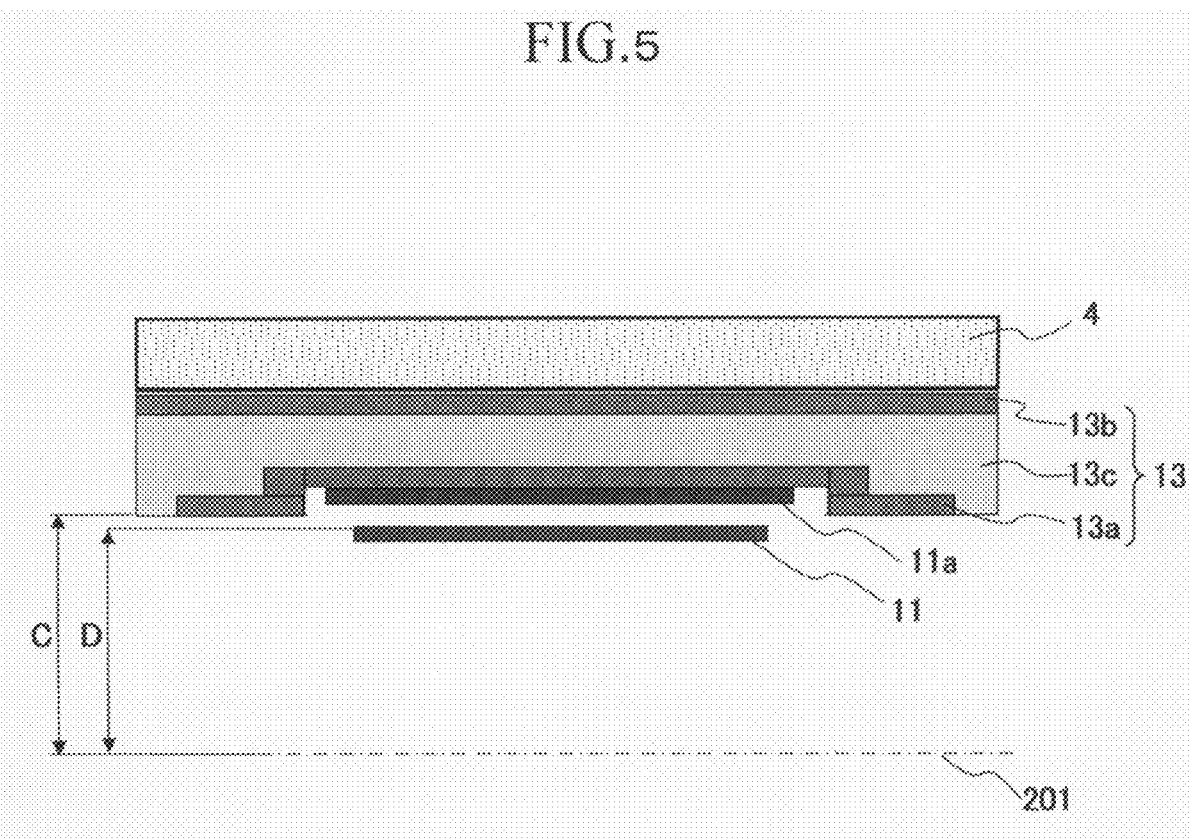
FIG. 5 is a diagram showing only a cross section of the upper side part of a horizontal magnetic field type MRI apparatus of short bore relating to embodiment 2.

FIG. 5 is a diagram showing only a cross section of an upper part of a horizontal magnetic field type MRI apparatus having a short bore relating to embodiment 2 of the present invention. In the present embodiment, out of the parts such as irradiation coil 11 and RF shield 11a that are configuring transmission system 3, external diameter (D) of cylindrical irradiation coil 11 is smaller than internal diameter (C) of cylindrical conductor portion 13f. As a result, only irradiation coil 11 is protruded from the concave of gradient magnetic field main coil 13a. To solve this problem, irradiation coil 11 can be easily disposed by sliding along gradient magnetic field main coil 13a from the outside of axis-direction of the gantry, though the improvement effect of the opened construction of the MRI apparatus is slightly reduced. The present embodiment has the advantage besides the one of embodiment 1 of improving the magnetic field generation efficacy by gradient magnetic field coil 13, since the spacing between gradient magnetic field main coil 13a and gradient magnetic field shielding coil 13b can be broadened compared to embodiment 1. Also, while intermediate member 13c is used to join gradient magnetic field main coil 13a and gradient magnetic field shielding coil 13b maintaining a predetermined spacing, it is possible to arrange in the inside of intermediate member 13c a shim coil, passive shim formed by material such as iron, or pipes for absorbing heat generated from gradient magnetic field coil 13.

Embodiment 3

Figure 6:
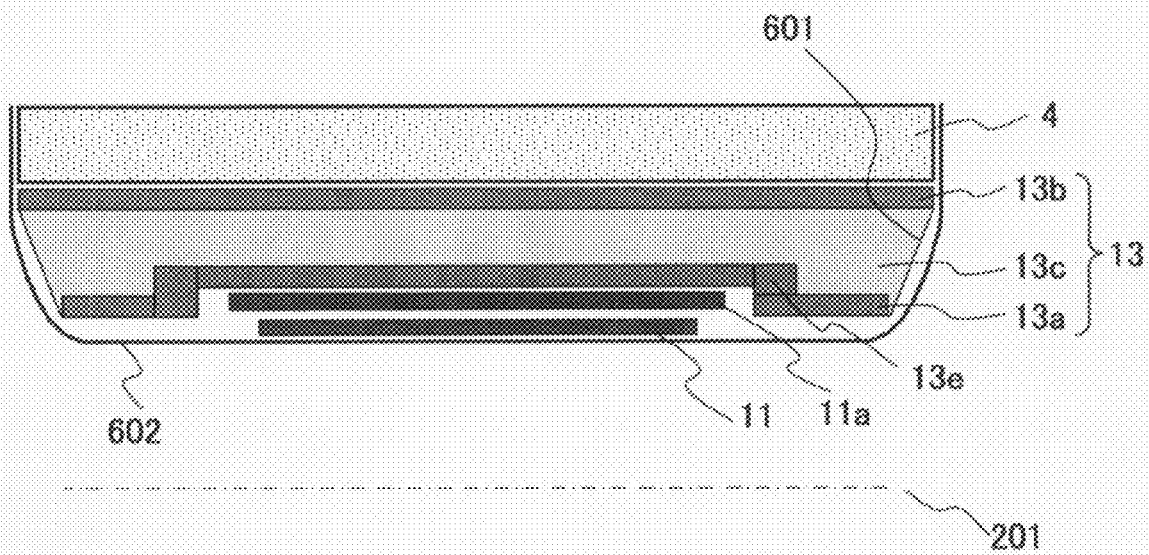
FIG. 6 is a diagram showing only a cross section of the upper side part of a horizontal magnetic field type MRI apparatus relating to embodiment 3.

FIG. 6 is a diagram showing only a cross section of the upper part of the horizontal magnetic field type MRI apparatus relating to embodiment 3 of the present invention. In an example of the present embodiment, compared to embodiment 2, the surface in end 601 of intermediate member 13c for joining gradient magnetic field main coil 13a and gradient magnetic shielding coil 13b is tapered, and width of intermediate member 13c is made narrower on the side of imaging space 202 than the side of magnet 4, in Z-axis 201 direction. By this configuration, the end portion of gantry cover 602 covering the whole magnet can be formed having a certain curvature. As a result, the opened construction of the MRI apparatus can be further improved in addition to the improvements described in embodiments 1 and 2.

Embodiment 4

Figure 7:
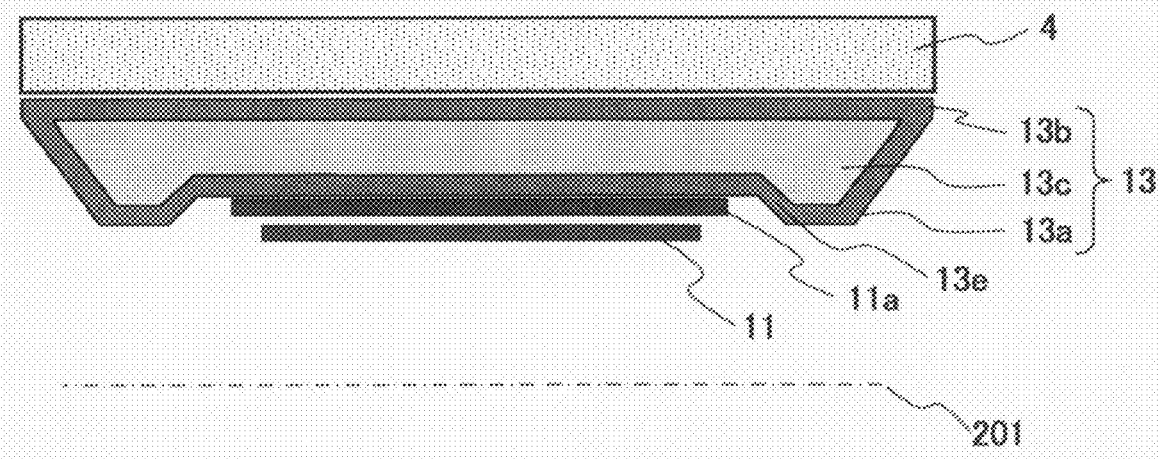
FIG. 7 is a diagram showing only a cross section of the upper side part of a horizontal magnetic field type MRI apparatus relating to embodiment 4.

FIG. 7 is a diagram showing only a cross section of the upper part of a horizontal magnetic field type MRI apparatus relating to embodiment 4 of the present invention. In the present embodiment, compared to embodiment 3, gradient magnetic field main coil 13a and gradient magnetic shielding coil 13b are continually joined on the outside of Z-axis 201 direction of intermediate member 13c.

As described in JP-A-H8-38457, other than advantages described in embodiments 1~3, the advantage of reducing the variable magnetic field with respect to the examinee is further attained by the present configuration, due to the acquisition of the effect of constraining the gradient magnetic field in the outside of the imaging region of the examinee.

Embodiment 5

Figure 8:
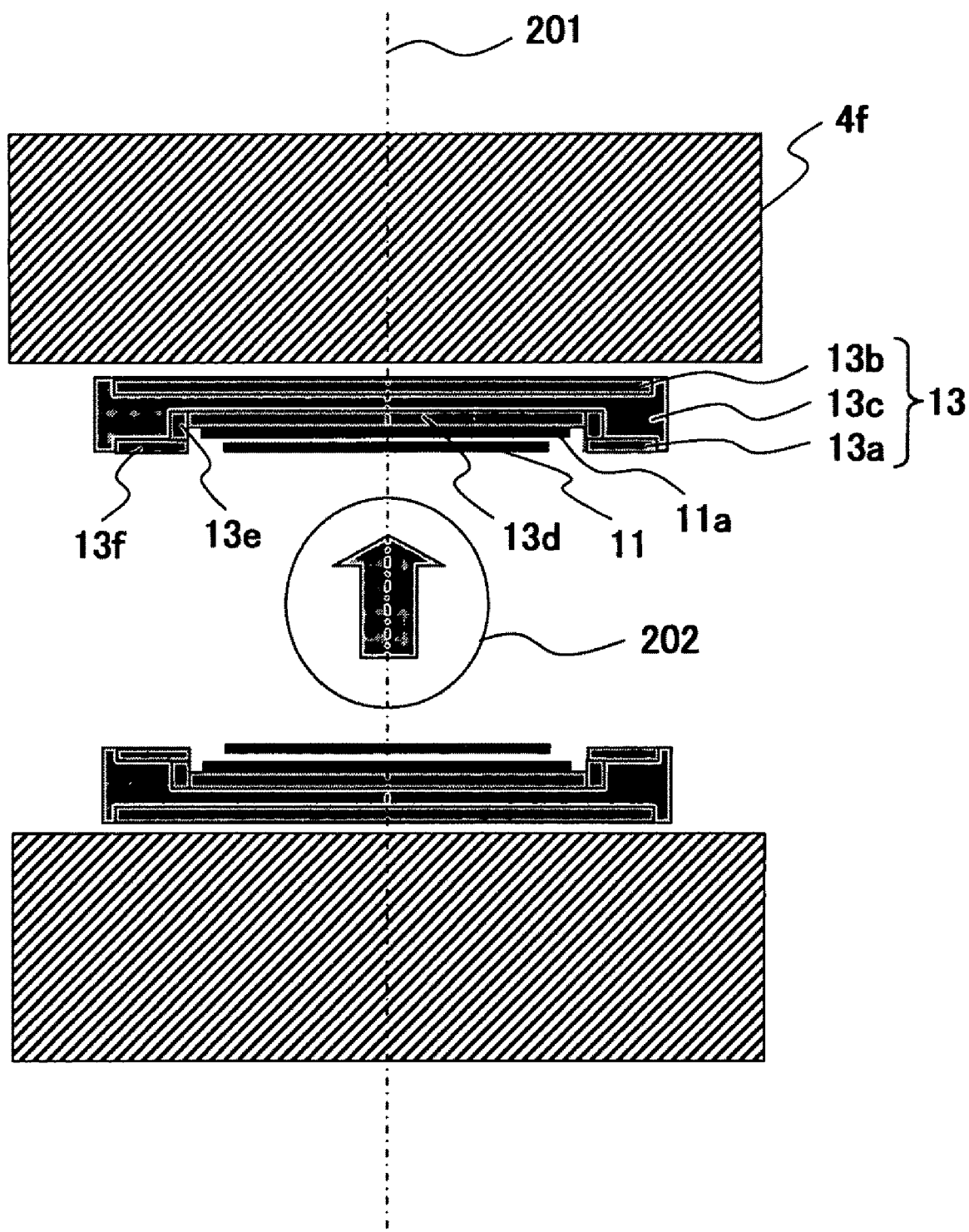
FIG. 8 is a diagram showing a cross section of a vertical magnetic field type MRI apparatus relating to embodiment 5.

FIG. 8 is a diagram showing a cross section of a vertical magnetic field type MRI apparatus (open type) relating to embodiment 5 in the present invention. In FIG. 8, 4f indicates the static magnetic field generation magnet arranged over and under the imaging space facing each other, and other numbers are the same as shown in FIG. 2 of embodiment 1. Difference is that the parts such as gradient magnetic field coil 13 or irradiation coil 11 shown in FIG. 8 in the present embodiment are not the combination of cylinder shape parts as in embodiments 1~4, but are in disk-like shape being conformed to the shape of the static magnetic field generation magnets in the vertical magnetic field type MRI apparatus (open type). In the present embodiment, the gradient magnetic field main coil is divided into an inside and outside portions with respect to the central axis of the static magnetic field, the inside is kept at a distance from imaging space (distanced toward the outside in vertical directions (up and down)), and at least a part of the irradiation coil and the like are contained therein. This configuration enables the enlargement of imaging space 202 for placing the examinee, whereby improving the open construction of the MRI apparatus.

The present invention is not limited to the above-mentioned embodiments, and various changes may be made without departing from the scope of the invention. For example, while the radius of gradient magnetic field main coil 13a is configured by cylindrical bottom portion 13d and end portion 13f formed by two kinds of internal radii, the kind of radius for the cylindrical shape with different size of internal radii may be more than 3 kinds. Also, in embodiment 5, the number for dividing the gradient magnetic field main coil with respect to the central axis is not limited to two (inside and outside), and may be more than 3. Also, technical features described in embodiments 1~4 can be applied to the vertical magnetic field type MRI apparatus illustrated in embodiment 5. The direction for disposing coupling portion 13e in FIG. 2 may be vertical to Z-axis as seen in FIG. 6, or it may be tilted as seen in FIG. 7. Also, it goes without saying that while the body axis of the examinee placed in the imaging space is Z-axis 201 in the horizontal magnetic field type MRI apparatus of embodiments 1~4, it is a horizontal direction vertical to Z-axis 201 in the vertical magnetic field type MRI apparatus in embodiment 5.

The invention claimed is:

1. A magnetic resonance imaging apparatus comprising:
   static magnetic field generation means arranged in the vicinity of an imaging space where an examinee is to be located, and generating a static magnetic field in the imaging space;
   gradient magnetic field generation means arranged in the imaging space side of the static magnetic field generation means and generating a gradient magnetic field in the imaging space; and
   high-frequency magnetic field generation means arranged at the imaging space side of the gradient magnetic field generation means and generating a high-frequency magnetic field in the imaging space,
   wherein the gradient magnetic field generation means has a concave portion at a center and surrounding part thereof, depressed toward the static magnetic field generation means, and at least a part of the high-frequency magnetic field generation means is contained in the concave portion.

2. The magnetic resonance imaging apparatus according to claim 1, wherein the concave portion has a cross section shaped in rectangle, and one side of the rectangle is parallel to the body axis of an examinee located in the imaging space.

3. The magnetic resonance imaging apparatus according to claim 1, wherein the concave portion has a trapezoidal shape, and the upper and lower hem of the trapezoid are parallel to the body axis of the examinee located in the imaging space.

4. The magnetic resonance imaging apparatus according to claim 1, wherein:
   the static magnetic field generation means has a cylindrical shape;
   the gradient magnetic field generation means is placed along the internal surface of the cylinder on the imaging space side of the static magnetic field generation means; and
   the concave portion is formed along the internal surface of the cylinder.

5. The magnetic resonance imaging apparatus according to claim 1, wherein:
   the gradient magnetic field generation means has a gradient magnetic field main coil for generating a main gradient magnetic field in the imaging space, and a gradient magnetic field shielding coil for preventing the magnetic field generated by the gradient magnetic field main coil from leaking to the other side of the imaging space;
   the gradient magnetic field main coil is formed by a first cylindrical portion having a first radius which has the same axis as the body axis of the examinee, a second cylindrical portion which has the smaller internal radius than the first internal radius and the same axis as the body axis of the examinee, and a coupling portion for connecting the first cylindrical portion and the second cylindrical portion; and
   the first cylindrical portion is placed on the side closer to the imaging space than the second cylindrical portion along the body axis direction of the examinee, and the high-frequency magnetic field generation means is placed on the imaging space side of the first cylindrical portion.

6. The magnetic resonance imaging apparatus according to claim 5, wherein the second cylindrical portion and the coupling portion are divided into two directions which are in one direction and the other direction with respect to the first cylindrical portion in the body axis direction of the examinee, and each of them are symmetrically imposed in one direction and the other direction with respect to the center of the imaging space in the body axis direction of the examiner.

7. The magnetic resonance imaging apparatus according to claim 5, wherein:
   the spacing between the gradient magnetic field main coil and the gradient magnetic field shielding coil is provided with an intermediate member for maintaining the spacing with predetermined intervals;
   the gradient magnetic field main coil is narrower in width than the gradient magnetic field shielding coil in the body axis direction of the examinee; and
   the most outside surface of the intermediate member in the body axis direction of the examinee is tilted with respect to the direction vertical to the body axis of the examinee while connecting the outside edges in the body axis direction of the gradient magnetic field main coil and the gradient magnetic field shielding coil having different length.

8. The magnetic resonance imaging apparatus according to claim 5, wherein the gradient magnetic field main coil and the gradient, magnetic field shielding coil are imposed by being continually connected at surfaces on the most outer side of the intermediate member in the body axis direction of the examinee.

9. The magnetic resonance imaging apparatus according to claim 5, wherein the gradient magnetic field main coil is configured such that a coil is attached to a container having a bump made by combining the cylinders having different size of radii.

10. The magnetic resonance imaging apparatus according to claim 9, characterized in that the center of coil pattern of the coil is placed in the vicinity of the bump.

11. The magnetic resonance imaging apparatus according to claim 5, wherein the coupling portion is vertically disposed in the body axis direction with respect to the examinee.

12. The magnetic resonance imaging apparatus according to claim 5, wherein the coupling portion is tilted with respect to the direction vertical to the body axis of the examinee.

13. The magnetic resonance imaging apparatus according to claim 1, wherein:
the static magnetic field generation means are arranged facing each other sandwiching an imaging space therebetween;
the gradient magnetic field generation means are arranged facing each other sandwiching the imaging space therebetween on the imaging side of the static magnetic field generation means; and
the concave portion is formed at the center and surrounding portion of internal surfaces of the gradient magnetic field generation means facing each other.

14. The magnetic resonance imaging apparatus according to 13, wherein:
the gradient magnetic field generation means is formed by a gradient magnetic field main coil for generating a main gradient magnetic field in the imaging space, and a gradient magnetic field shielding coil for preventing the magnetic field generated by the gradient magnetic field main coil from leaking to the other side of the imaging space;
the gradient magnetic field main coil is formed by the inside portion and outside portion with respect to the central axis of the static magnetic field, and the coupling portion for connecting the inside and outside portions; and
the inside portion is imposed more on the outside with respect to the imaging space in opposed directions than the outside portions, and the high-frequency magnetic field generation means is disposed on the imaging space side of the inside portion.

15. The magnetic resonance imaging apparatus according to claim 1, wherein:
high-frequency magnetic field generation means is formed in 2 layers, of which one layer is arranged on the imaging space side and is an RF coil formed by a conductor or condenser element, and the other layer is an RF shield arranged on the gradient magnetic field generation means side; and
the RF coil and RF shield are maintained at predetermined intervals by an intermediate member for the high-frequency magnetic field generation means.

16. The magnetic resonance imaging apparatus according to claim 15, wherein the RF coil is arranged on the outside of the concave portion, and is enabled to be imposed by sliding it to the body axis direction of the examinee.

17. The magnetic resonance imaging apparatus according to claim 15, wherein the RF coil, RF shield and intermediate member for high-frequency magnetic field generation means are segmented and contained in the concave portion.

18. The magnetic resonance imaging apparatus according to claim 1, wherein the concave portion is at a central portion of the gradient magnetic field generation means relative to a Z-axis or body axis of the examinee.

19. A magnetic resonance imaging apparatus comprising:
static magnetic field generation means arranged in a vicinity of an imaging space where an examinee is to be located, and generating a static magnetic field in the imaging space;
gradient magnetic field generation means arranged in the imaging space side of the static magnetic field generation means and generating a gradient magnetic field in the imaging space; and
high-frequency magnetic field generation means arranged at the imaging space side of the gradient magnetic field generation means and generating a high-frequency magnetic field in the imaging space,
wherein an internal radius of a center portion of the gradient magnetic field generation means is larger than an internal radius of another portion near an end side of the gradient magnetic field generation means, and at least a part of the high-frequency magnetic field generation means is contained in the central portion.

* * * * *